(12) United States Patent
Berry et al.

(10) Patent No.: US 7,777,085 B2
(45) Date of Patent: Aug. 17, 2010

(54) METHOD FOR CONVERSION OF OIL-CONTAINING ALGAE TO 1,3-PROPANEDIOL

(75) Inventors: William W. Berry, Lakeland, FL (US); Mark G. Tegen, Gig Harbor, WA (US); William R. Sutterlin, Columbia, MO (US)

(73) Assignee: Inventure Chemical, Inc., San Francisco, CA (US)

( * ) Notice: Subject to any disclaimer, the term of this patent is extended or adjusted under 35 U.S.C. 154(b) by 0 days.

(21) Appl. No.: 12/243,936

(22) Filed: Oct. 1, 2008

(65) Prior Publication Data

US 2010/0081181 A1 Apr. 1, 2010

(51) Int. Cl.
*C07C 29/149* (2006.01)
*C07C 29/147* (2006.01)
(52) U.S. Cl. .................................. 568/864
(58) Field of Classification Search ............ 568/864
See application file for complete search history.

(56) References Cited

U.S. PATENT DOCUMENTS

| | | | |
|---|---|---|---|
| 2,383,601 A | 8/1945 | Keim | |
| 2,434,110 A | 1/1948 | Hatch et al. | |
| 2,494,366 A | 1/1950 | Sprules et al. | |
| 3,068,303 A | 12/1962 | Pattison | |
| 3,098,882 A | 7/1963 | Arnold | |
| 3,109,804 A | 11/1963 | Martin | |
| 3,205,281 A | 9/1965 | Fleming et al. | |
| 3,260,759 A | 7/1966 | Skinner | |
| 3,296,325 A | 1/1967 | Gross et al. | |
| 3,916,031 A | 10/1975 | Beal | |
| 4,164,506 A | 8/1979 | Kawahara et al. | |
| 4,280,962 A | 7/1981 | Watanabe et al. | |
| 4,665,158 A | 5/1987 | Armanet et al. | |
| 4,695,411 A | 9/1987 | Stern et al. | |
| 4,698,186 A | 10/1987 | Jeromin et al. | |
| 4,874,893 A | 10/1989 | Flork | |
| 4,912,260 A | 3/1990 | Dobson et al. | |
| 5,015,789 A | 5/1991 | Arntz et al. | |
| 5,093,537 A | 3/1992 | Unruh et al. | |
| 5,180,597 A | 1/1993 | Hamm | |
| 5,210,318 A | 5/1993 | Briggs et al. | |
| RE34,349 E | 8/1993 | Unruh et al. | |
| 5,256,827 A | 10/1993 | Slaugh et al. | |
| 5,298,637 A | 3/1994 | Cooper | |
| 5,334,778 A | 8/1994 | Haas et al. | |
| 5,358,633 A | 10/1994 | Dai et al. | |
| 5,364,984 A | 11/1994 | Arntz et al. | |
| 5,382,715 A | 1/1995 | Vargas et al. | |
| 5,389,595 A | 2/1995 | Simpson et al. | |
| 5,399,793 A | 3/1995 | Vargas et al. | |
| 5,449,653 A | 9/1995 | Briggs et al. | |
| 5,455,370 A | 10/1995 | Demmering et al. | |
| 5,475,134 A | 12/1995 | Baker | |
| 5,525,126 A | 6/1996 | Basu et al. | |
| 5,596,085 A | 1/1997 | Silver et al. | |
| 5,773,657 A | 6/1998 | Rutter et al. | |
| 5,786,524 A | 7/1998 | Powell et al. | |
| 5,814,112 A | 9/1998 | Elliott et al. | |
| 5,817,594 A | 10/1998 | McNamara et al. | |
| 5,888,380 A | 3/1999 | Fujita et al. | |
| 5,910,241 A | 6/1999 | McNamara et al. | |
| 5,916,838 A | 6/1999 | Wulff-Doring et al. | |
| 5,936,126 A | 8/1999 | Ruhl et al. | |
| 5,945,570 A | 8/1999 | Arhancet et al. | |
| 5,958,825 A | 9/1999 | Wulff-Doring et al. | |
| 5,972,118 A | 10/1999 | Hester et al. | |
| 5,977,013 A | 11/1999 | Elliott et al. | |
| 6,093,845 A | 7/2000 | van Acker et al. | |
| 6,152,975 A | 11/2000 | Elliott et al. | |
| 6,232,511 B1 | 5/2001 | Haas et al. | |
| 6,342,464 B1 | 1/2002 | Arhancet et al. | |
| 6,376,720 B1 | 4/2002 | Han | |
| 6,399,538 B1 | 6/2002 | Hucul | |
| 6,399,800 B1 | 6/2002 | Haas et al. | |
| 6,423,857 B1 | 7/2002 | Copeland et al. | |
| 6,429,167 B1 | 8/2002 | Maeno et al. | |
| 6,432,469 B1 | 8/2002 | Remmereit et al. | |
| 6,660,506 B2 | 12/2003 | Nguyen et al. | |
| 6,670,300 B2 | 12/2003 | Werpy et al. | |
| 6,768,015 B1 | 7/2004 | Luxem et al. | |
| 6,855,838 B2 | 2/2005 | Haas et al. | |
| 6,911,566 B2 | 6/2005 | Tsunoda et al. | |
| 6,933,398 B2 | 8/2005 | Peter et al. | |
| 6,965,044 B1 | 11/2005 | Hammond et al. | |
| 7,449,313 B2 | 11/2008 | Rush | |
| 2002/0077492 A1 | 6/2002 | Goto et al. | |
| 2002/0087036 A1 | 7/2002 | Haas et al. | |
| 2003/0158074 A1 | 8/2003 | Haas et al. | |
| 2003/0229237 A1 | 12/2003 | Haas et al. | |
| 2004/0059143 A1 | 3/2004 | Peter et al. | |
| 2004/0097764 A1 | 5/2004 | Tsunoda et al. | |
| 2004/0182749 A1 | 9/2004 | Domokos et al. | |
| 2004/0225161 A1 | 11/2004 | Sunkara et al. | |
| 2004/0260125 A1 | 12/2004 | Seapan et al. | |
| 2005/0020842 A1 | 1/2005 | Haas et al. | |

(Continued)

FOREIGN PATENT DOCUMENTS

CN 1342521 4/2002

(Continued)

OTHER PUBLICATIONS

Ben-Amotz, Ami et al. "Chemical Profile of Selected Species of Microalgae with Emphasis on Lipids," J.Phycol. 21, 72-81 (1985).

(Continued)

*Primary Examiner*—Elvis O Price
(74) *Attorney, Agent, or Firm*—Frommer, Lawrence & Haug LLP; Shelly M. Fujikawa; John W. Branch

(57) ABSTRACT

The present invention relates to a process for oxidizing renewable polyunsaturated fatty acids eicosapentaenoic acid (EPA) and docosahexaenoic acid (DHA) to a malonic acid intermediate which is subsequently reduced to 1,3 propanediol (PDO).

20 Claims, 5 Drawing Sheets

U.S. PATENT DOCUMENTS

| | | |
|---|---|---|
| 2005/0033099 A1 | 2/2005 | Ryu et al. |
| 2005/0080300 A1 | 4/2005 | Komplin et al. |
| 2005/0112735 A1 | 5/2005 | Zappi et al. |
| 2005/0274065 A1 | 12/2005 | Portnoff et al. |
| 2006/0155138 A1 | 7/2006 | Haas et al. |
| 2007/0100162 A1 | 5/2007 | Petrus et al. |
| 2007/0232817 A1 | 10/2007 | Pereira et al. |
| 2008/0051593 A1 | 2/2008 | Berry et al. |
| 2008/0160593 A1 | 7/2008 | Oyler |
| 2009/0071064 A1 | 3/2009 | Machacek et al. |

FOREIGN PATENT DOCUMENTS

| | | |
|---|---|---|
| CN | 1342633 | 4/2002 |
| CN | 1428190 | 7/2003 |
| CN | 1428322 | 7/2003 |
| CN | 1699516 | 11/2005 |
| FR | 2191939 | 2/1974 |
| GB | 829475 | 3/1960 |
| GB | 966270 | 8/1964 |
| GB | 1011270 | 11/1965 |
| GB | 1436458 | 5/1976 |
| GB | 2015509 | 9/1979 |
| GB | 1581379 | 12/1980 |
| GB | 2073232 | 10/1981 |
| JP | 54084508 | 7/1979 |
| JP | 2004182622 | 7/2004 |
| WO | WO-9745390 | 12/1997 |
| WO | WO-0000456 | 1/2000 |
| WO | WO-02074881 | 9/2002 |
| WO | WO-03085070 | 10/2003 |
| WO | WO-2004103934 | 12/2004 |
| WO | WO-2005058856 | 6/2005 |
| WO | WO-2006116193 | 11/2006 |
| WO | WO-2008086495 | 7/2008 |
| WO | WO-2008122029 | 10/2008 |

OTHER PUBLICATIONS

Hudson, Bertram et al. "The Lipids of the Alga *Spirulina*," J.Sci.Fd Agric. 1974, 25, 759-763.

Suen, Yu et al. "Total Lipid Production of the Green Alga *Nannochloropsis* Sp. QII Under Different Nitrogen Regimes," J.Phycol. 23, 289-296 (1987).

Sheehan, John et al. "A Look Back at the U.S. Department of Energy's Aquatic Species Program—Biodiesel from Algae," National Renewable Energy Laboratory, Jul. 1998 (328 pgs.).

Aldrich Handbook of Fine Chemicals and Laboratory Equipment, 2000-2001, title page, pp. 1012, 1252, 1266, 1521.

Boldizsar, I. et al., "Simultaneous GC-MS Quantitation of Acids and Sugars in the Hydrolyzates of Immunostimulant, Water-Soluble Polysaccharides of Basidiomycetes," Chromatographia, 1998, Accession No. 1998:300996 CAPLUS, 47(7/8):413-419.

Canakci, M. et al., "Biodiesel Production from Oils and Fats with High Free Fatty Acids," Abstracts of the 92.sup.nd American Oil Chemists' Society Annual Meeting and Expo, p. S74 (2001).

Foglia, T. A., et al., "Quantitation of Neutral Lipid Mixtures Using High Performance Liquid Chromatography with Light Scattering Detection," Journal of Lipquid Chrom. & Rel. Technol., vol. 20 (12):1829-1838 (1997).

Freedman, B., et al., "Variables Affecting the Yields of Fatty Esters from Transesterified Vegetables Oils," J. Am. Oil Chem. Soc. vol. 61(10) 1638-1643, Oct. 1984.

Graboski, M. S., et al., "Combustion of Fat and Vegetable Oil Derived Fuels in Diesel Engines," Prog. Energy Combust. Sci., vol. 24, pp. 125-164 (1998).

Haas, M. J., et al., "Enzymatic Approaches to the Production of Biodiesel Fuels," Lipid Biotechnology (Marcel Dekker, Inc., New York), 2002, pp. 587-598.

Haas, M. J., et al., "Engine Performance of Biodiesel Fuel Prepared from Soybean Soapstock: A High Quality Renewable Fuel Produced from a Waste Feedstock," Energy & Fuels, 2001, 15(5):1207-1212.

Harrington, Kevin J., et al., "Transesterification in Situ of Sunflower Seed Oil," Ind. Eng. Chem. Prod. Dev., 1985, 24:314-318.

Hui, Y. H., "Bailey's Industrial Oil and Fat Products," Edible Oil and Fat Products: Processing Technology (John Wiley Sons, Inc., New York), 1996, 5th Edition, vol. 4, pp. 56-57.

Kildiran, Gokhan et al., "In-Situ Alcoholysis of Soybean Oil," JAOCS, 1996, 73(2):225-228.

Krawczyk, T., "Biodiesel," Inform, Aug. 1996, 7(8):801, 804-808, 810.

Lewis, Richard J., Sr., editor, "Hawley's Condensed Chemical Dictionary," (Von Nostrand Reinhold Company: New York), 12th Edition, 1993, title page, bibliography page, pp. 34, 507.

Mittlebach, Martin, et al., "Diesel Fuel Derived from Vegetable Oils, III. Emission Tests Using Methyl Esters of Used Frying Oil," J. Am. Oil Chem. Soc., Jul. 1998, 65(7):1185-1187.

Swern, Daniel, "Bailey's Industrial Oil and Fat Products," 1982, 4th Edition, vol. 2, pp. 290-292.

Peterson, C. L., et al., Processing, Characterization, and Performance of Eight Fuels from Lipids, Applied Engineering in Agriculture, 1997, 13(1):71-79.

Singer, Brian, et al., "The Simultaneous Analysis of Proteins, Lipids, and Diterpenoid Resins Found in Cultural Objects," Annali di Chimica (Rome, Italy), 2007, 97(7):405-417.

Standard Specification for Biodiesel Fuel (B100) Blend Stock for Distillate Fuels, Designation D 6751-02, American Society for Testing and Materials, West Conshohocken, PA, 2002.

Huber, G. W., et al., "Synthesis of Transportation Fuels from Biomass: Chemistry, Catalysts, and Engineering," American Chemical Society, 106(9):4044-4098, Sep. 2006.

Sanders et al. "Bio-Refinery as the Bio-Inspired Process to Bulk Chemicals, " Feb. 13, 2007, Macromol Biosci, vol. 7, pp. 105-117 (13 pgs).

Simple Example of the chemistry

Seperate the malonic acid. Notice you should get 4 molecules of malonic acid.

Or you may have to go through the ester.

METHOD FOR CONVERSION OF OIL-CONTAINING ALGAE TO 1,3-PROPANEDIOL

FIELD OF THE INVENTION

The present invention relates to a process for generating unsaturated fatty acid alkyl esters from algae, optionally hydrolyzing the unsaturated fatty acid alkyl esters to unsaturated fatty acids, and oxidizing the unsaturated fatty acids alkyl esters or unsaturated fatty acids to malonic acid which is subsequently reduced to 1,3-propanediol (1,3-PDO).

BACKGROUND OF THE INVENTION 1,3-propanediol (1,3-PDO) is a compound having multiple uses. It is used as a chemical intermediate and in plastics, resins, fibers and coatings. For example, it is used as a monomer unit in the production of polyesters and polyurethanes that are useful as films and as fibers for carpets and textiles. It is also useful as an engine coolant.

1,3-PDO, when derived from petroleum sources, may be prepared from ethylene oxide (EO) in a process involving two primary reactions. First, EO and synthesis gas ($H_2/CO$) are catalytically hydroformylated to form 3-hydroxypropional-dehyde (HPA) in an organic solvent. The HPA is extracted from the solvent with water to form an aqueous solution of HPA, and the aqueous solution of HPA is then hydrogenated in the presence of a catalyst to form 1,3-PDO.

Thus, the reactants in the primary industrial pathway to 1,3-PDO are petroleum sources which are imported from politically volatile areas, expensive and non sustainable for industrial chemical production. There is a need in the art for alternative methods for the production of 1,3-PDO that are reliable, inexpensive, and sustainable.

BRIEF SUMMARY OF THE INVENTION 1,3-propanediol is produced from algae as follows: (a) generating an unsaturated fatty acid alkyl ester by reacting the algae and an alcohol at a pH in a range of 0 to 7, at a temperature in a range of 140° C. to 300° C., and at a pressure in a range of 500 psig to 2800 psig, (b) optionally hydrolyzing the unsaturated fatty acid alkyl ester to an unsaturated fatty acid, (c) oxidizing the unsaturated fatty acid alkyl ester or the unsaturated fatty acid to generate malonic acid, and (d) reducing the malonic acid to generate 1,3-propanediol. The unsaturated fatty acid can be eicosapentaenoic acid (EPA), docosahexaenoic acid (DHA), or a combination thereof.

1,3-propanediol can also be produced from algae as indicated above with the additional step of reacting the malonic acid with an alcohol and an acid catalyst to form malonic diester followed by reducing the malonic diester to generate 1,3-propanediol.

BRIEF DESCRIPTION OF THE DRAWINGS

DETAILED DESCRIPTION OF THE INVENTION 1,3-PDO can be generated from the renewable source, algae, in a cost competitive pathway. As shown in FIG. 1, unsaturated fatty acid alkyl esters (304) are generated from algae (301) followed by the optional hydrolysis of the esters to form unsaturated fatty acids, the selective oxidation (311) of the unsaturated fatty acids or unsaturated fatty acid alkyl esters (310) to create malonic acid (312, 322), the optional esterification (313) of the malonic acid to form malonic diester (318), and the subsequent reduction (319, 323) of the malonic acid (322) or malonic diester (318) to 1,3-PDO (321, 328). The present invention is in contrast to traditional methods for producing 1,3-PDO from petroleum sources that are non-renewable, expensive, and from politically unstable areas.

Sources of Unsaturated Fatty Acids Alkyl Esters

Sources for unsaturated fatty acid alkyl esters for use in the present invention include traditional farm crops and non-food crops such as microalgae. Microalgae can yield up to 200 times the mass per acre per year as compared to a traditional farm crop such as soy beans. Moreover, microalgae are not a traditional food source, can be grown in salt water and do not require traditional farm land for production. Types of microalgae include nannochloropsis, skeletonema and chlorella and contain up to 50% of their overall lipid mass as eicosapentaenoic acid (EPA) and docosahexaneoic acid (DHA) lipids. The algae can be fresh or salt water algae, prokaryotic algae, or cyanobacteria. Various algae growing processes include growing algae in the presence of $CO_2$ from a power plant or other major $CO_2$ producing stack gases. Commercial suppliers of algae include Solix (Ft. Collins, Colo.), Seambiotic (Tel Aviv, Israel), and Greenfuels (Cambridge, Mass.).

Figure 1:
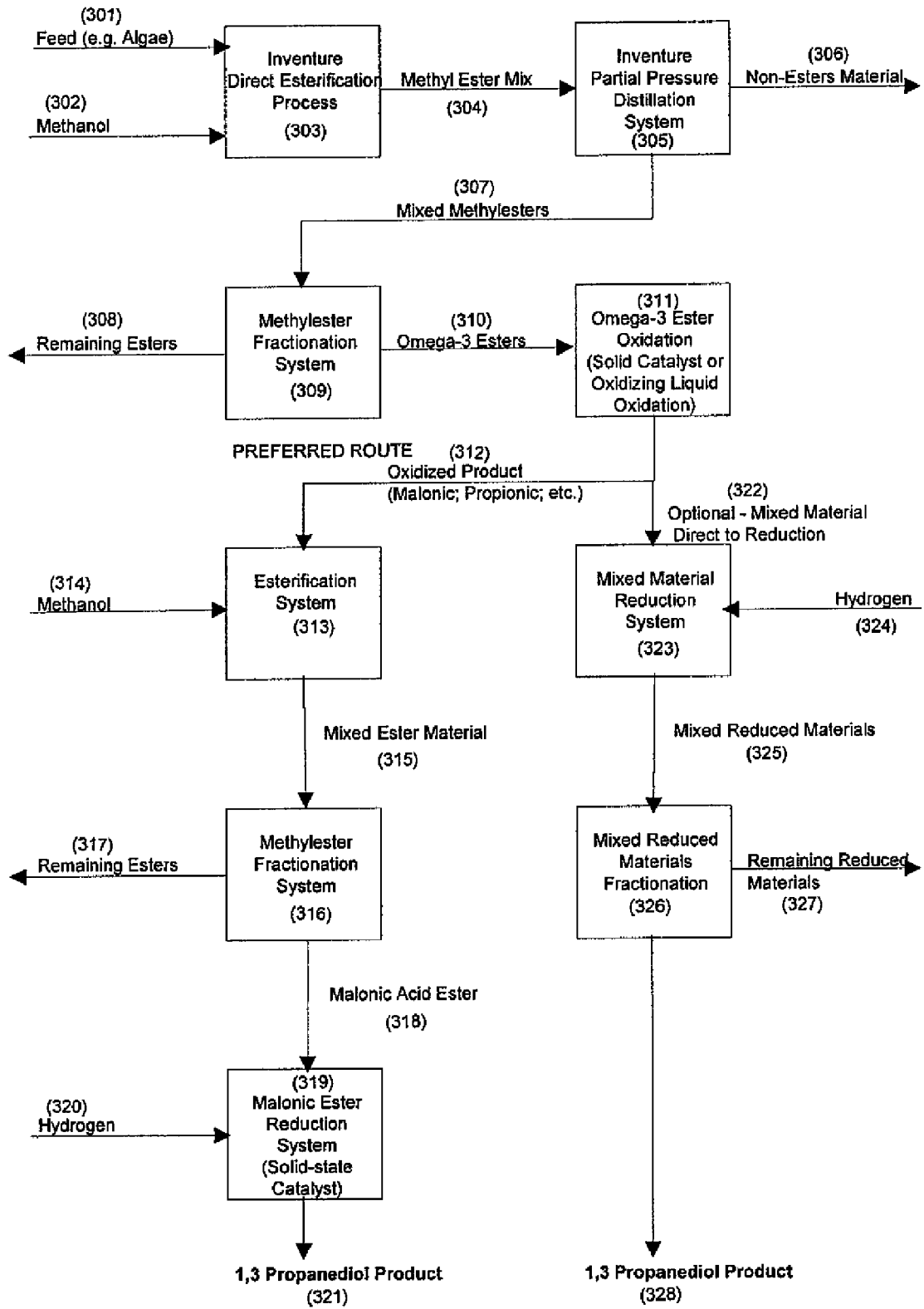
FIG. 1 provides an overview of the production of 1,3-PDO from a feedstock such as algae.
Figure 2:
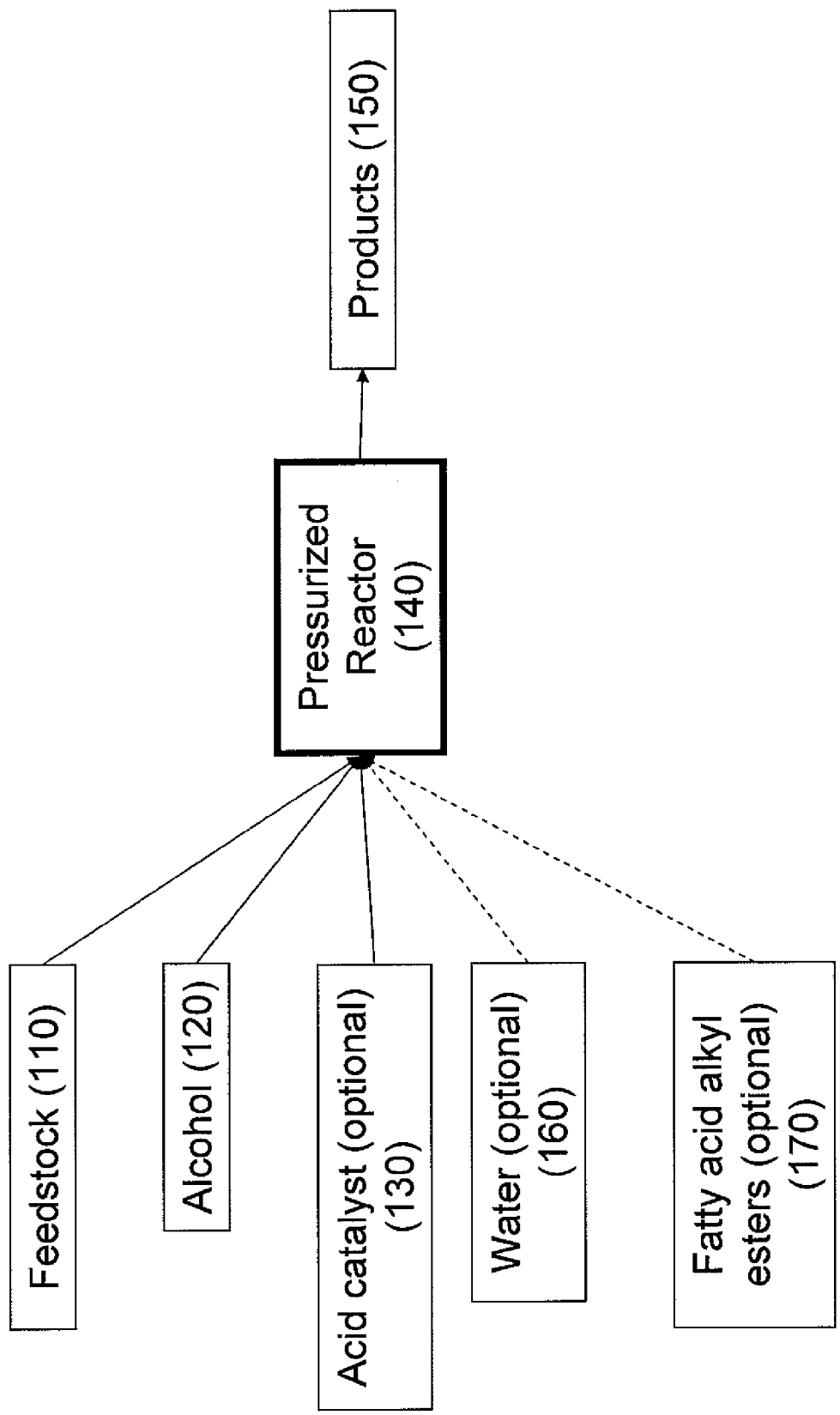
FIG. 2 provides a schematic of the reaction of the algae (110) with the alcohol (120) in the optional presence of the acid catalyst (130) and optionally in the presence of water (160) and fatty acid alkyl esters (170) in a pressurized reactor (140) to yield products (150).

The source of unsaturated fatty acid esters, e.g., algae, can include free fatty acids (FFAs), monoglycerides, diglycerides, triglycerides, phospholipids, or a combination thereof and can be reacted with alcohol optionally in the presence of an acidic catalyst to yield biodiesel (including unsaturated fatty acid alkyl esters) as described in U.S. patent application Ser. No. 12/061,038 assigned to Inventure Chemicals, Inc. and a U.S. Patent Application entitled "Production of biodiesel, cellulosic sugars, and peptides from the simulateoud esterification and alcoholysis/hydrolysis of materials with oil-containing substituents including phospholipids and cellulosic and peptidis content" filed Oct. 1, 2008 both incorporated by reference in their entireties herein. The source of unsaturated fatty acid esters, e.g., algae, can also include cellulosic material, proteins, or both that are transformed via alcoholysis, hydrolysis or both into cleaved cellulosic material, shortened proteins, amino acids, or a combination thereof as also described in as also described in these two U.S. patent applications. FIG. 2 illustrates the reaction in which algae feedstock (110) is reacted with alcohol (120) in the presence of an optional acid catalyst (130) and optionally in the presence of water (160) and fatty acid alkyl esters (170) in a pressurized reactor to yield products (150).

The algae can contain from about 0 wt % to about 100 wt % phospholipids, e.g., from about 5 wt % to about 50 wt % phospholipids. The algae can contain from about 0 wt % to about 50 wt % FFA and from about 50 wt % to about 100 wt % glycerides. The algae can also contain from about 0 wt % to about 50 wt % cellulosic material (preferable less than about 30 or 40 wt %, but at least about 1, 5, 10, or 15 wt %) and from about 0 wt % to about 50 wt % protein (preferable less than about 30 wt %, but at least about 1, 5, 10, or 15 wt %). Each of the amounts for the algae components listed above is based on the dry weight of the algae.

The algae for use in the reaction to form unsaturated fatty acid alkyl esters can be unextracted meaning that the algae have not been purified to remove particular components (e.g., water, cellulosic material, proteins, or mixtures thereof). For example, the algae can contain FFAs, glycerides, phospholipids, at least about 10 wt % cellulosic material, and at least about 10 wt % proteins, wherein both weight percentages are based on the total dry weight of the algae. The algae, prior to reaction, can be dried as, e.g., discussed below. The algae can be ground to reduce its particle size prior to reaction. For purposes of this discussion, algae is used as the unsaturated fatty acid alkyl ester source, however those skilled in the art would understand that other sources can be used.

The alcohol for the reaction can be, for example, methanol, ethanol, propanol, butanol, isopropyl alcohol, sec-butanol, t-butanol, benzyl alcohol or combination thereof. From a practical standpoint, and for general fuel and potential downstream chemical considerations, alcohols containing from 1 to 5 carbons would be preferred, however, there may be specific situations and conditions wherein higher alcohols could be used. Testing with a specific alcohol would readily determine the amenability of a particular alcohol. For purposes of this discussion, methanol is used as the alcohol, however those skilled in the art would understand that other alcohols can be used.

The optional acid catalyst for the reaction can be, for example, an inorganic acid (e.g., sulfuric acid, anhydrous hydrochloric acid, anhydrous nitric acid, boron trifluoride, and phosphoric acid), an organic acid (e.g. organic sulfonic acid), a solid phase catalyst (e.g., Envirocat™ EPZG, natural kaolinite clay, $B_2O_3/ZrO_2$, sulfated $SnO_2$, and zeolites), or combination thereof. For the purposes of this description, sulfuric acid is used as the acid catalyst, however those skilled in the art will understand that other acid catalysts can be used.

Figure 3:
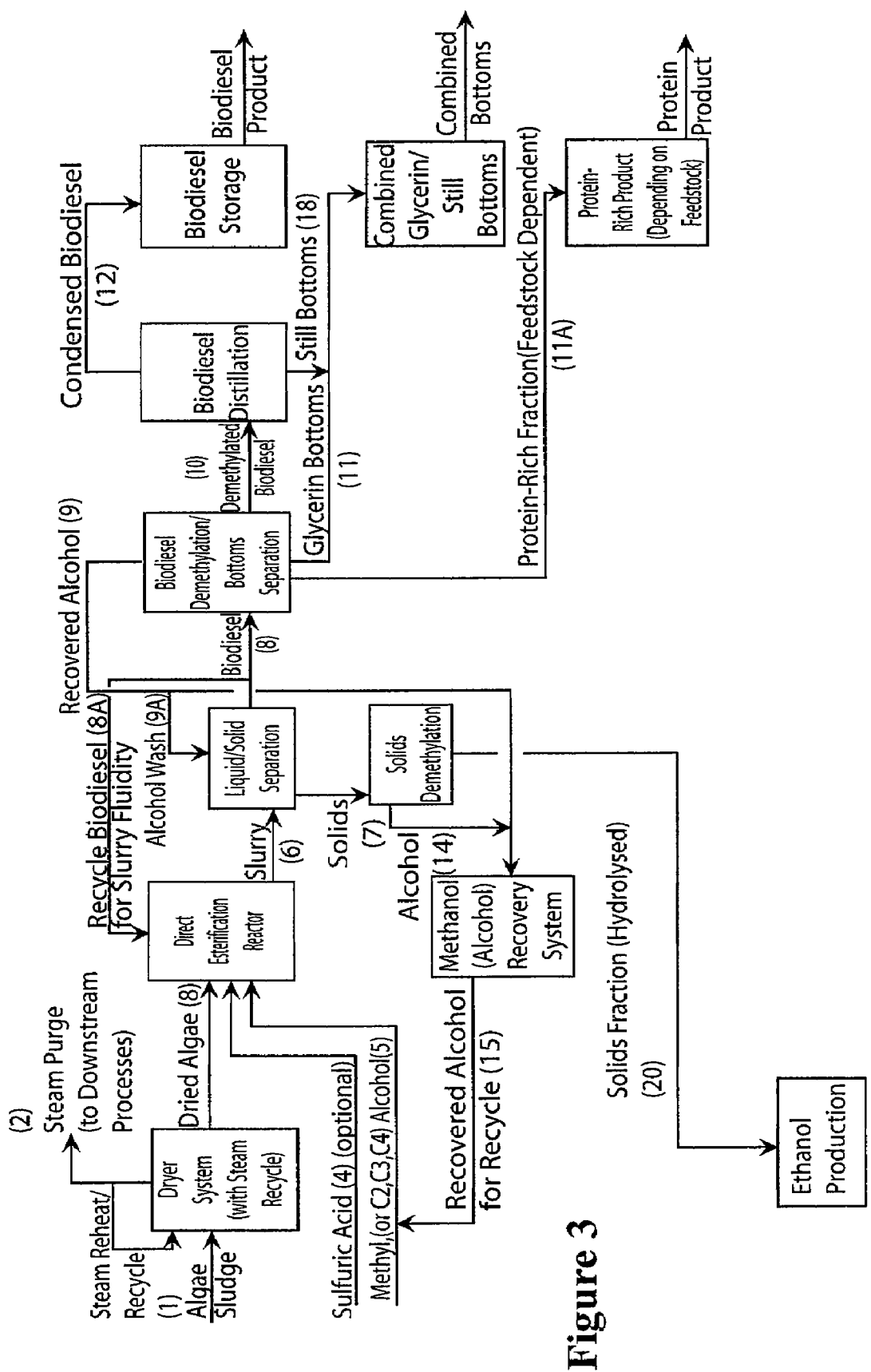
FIG. 3 shows the detailed process concept used for the simultaneous production of biodiesel (i.e., fatty acid alkyl esters), peptides, and ethanol from the algae. If dry material is received, then the front end drying system would not necessarily be required.

In the process (see FIG. 3), the algae sludge (1) is first dried in a flash drying system wherein a recycled stream of superheated steam is used to dry the algae. In at least some embodiments, the water content of the algae feedstock after drying can be about 0 wt % to about 10 wt % of the dry weight of the feedstock, from about 3 wt % to about 10 wt % of the dry weight of the feedstock, or from about 3 wt % to about 5 wt % dry weight of the feedstock. The resulting steam, from the wet material, is purged from the system (2) and used for downstream process heat.

Systems that are useful for this step include spin flash dryers; spray dryers; loop dryers; and the like. The main criterion for dryer choice is that the system can be operated at elevated pressure to allow for production of reasonably usable purge steam. A pressure of 10 psig to 30 psig is preferred with 15 psig to 20 psig most preferred. Drying can be carried out at atmospheric pressure, however, in this case the resulting vapor from the dryer cannot be reused for downstream steam uses. Pressurized drying enhances the overall economics of the process, but is not essential for practice of the technique, i.e. atmospheric drying is acceptable, recognizing the economics of the system.

The dried algae (3) can be ground to reduce its particle size and is then transferred to the Direct Esterification Reactor system wherein the feedstock is mixed with the selected alcohol (e.g., methanol) (5), and an optional acid catalyst (4). The amount of alcohol can vary, but would typically be sufficient to allow for a slurry mixture. This typically provides sufficient excess of alcohol for the reaction noting that 3 moles of alcohol are required for reaction with 1 mole of triglycerides to form 3 moles of fatty acid alkyl esters and 1 mole of alcohol is required for reaction with 1 mole of FFAs to form 1 mole of fatty acid alkyl esters. In at least some embodiments, the amount of alcohol should be in about a 15% molar excess of the contained oil. Preferably, the alcohol should be in an amount from about 50 mol % to about 600 mol % of the contained oil (i.e., glycerides, FFAs, phospholipids, or a combination thereof), preferably from about 50 mol % to about 320 mol % of the contained oil and most preferably from about 200 mol % to about 300 mol % of the contained oil. On a weight percentage basis, the contained oil will require about 11% to 12% by weight of methanol to form the methyl ester. Higher alcohols would require a higher weight percentage of alcohol. For practical operation, the amount of alcohol would normally be in the range of about 50 wt % to 300 wt % of the dry feedstock and preferably in the range of about 100 wt % to about 200 wt % of the dry feedstock.

To reduce the amount of alcohol used, and subsequently reduce the downstream demethylation requirements, a portion of the produced biodiesel (8A) can be recycled to the reactor to provide liquid for slurry formation. The amount of fatty acid alkyl ester (i.e., biodiesel) added to the reaction can be in an amount from about 50 wt % to about 300 wt %, preferably from about 100 wt % to about 200 wt %, and most preferably from about 125 wt % to about 150 wt % of the dry weight of the feedstock. This will allow for introduction of alcohol in amounts sufficient to provide the amount required for the reaction, plus some excess to ensure complete reaction. In this case, the amount of make-up alcohol (e.g. methanol) could be in the range of 5% to 15% by weight of the dry input feedstock.

The amount of optional acid catalyst can range from about 0% to about 15% by weight of the dry algae feedstock, preferably from about 3% to about 9% by weight of the dry feedstock, and most preferably from about 4% to about 8% by weight of the dry feedstock. The final amount of acid will depend on the composition of the feedstock, since there may be acid consuming compounds in the feed, e.g., reactive protein materials and the like. Thus the actual acid rate will depend on this factor. From a general process consideration standpoint, the key process factor is the amount of "free catalyst" in the system, i.e. free acid after consideration of any components in the feedstock that will consume acid. Preferably the amount of free acid remaining in the mixture is such that the resulting pH of the slurry is in the range of about 0 to about 5, preferably from about 1 to about 4, and most preferably in the range of about 2 to about 3.

In the presence of acid catalyst, the reaction temperature is, e.g. in the range of about 140° C. to about 300° C., in the range of about 160° C. to about 275° C., in the range of about 175° C. to about 275° C. A pressure reactor system is used that will allow for the elevated temperature and keep the alcohol from boiling in the presence of acid catalyst. The pressure of reactor operation is slightly in excess of the vapor pressure of the alcohol of choice at the selected operating temperature (e.g. 20 psig over the vapor pressure). Typical pressures ranges for a reaction in the presence of acid catalyst are from about 150 psig to about 650 psig, preferably from about 200 psig to about 500 psig, and most preferably from about 300 psig to about 400 psig. Pressures significantly in excess of the alcohol vapor pressure are not required in the process approach.

In the absence or reduction of acid catalyst (e.g., in the range from about 0.01 to 1 wt % based on the dry weight of the feedstock), the temperature of the reaction is increased to a range of about 240° C. to about 300° C., about 240° C. to about 270° C., or about 250° C. to about 280° C. The pressure of the reaction in the absence of acid catalyst is increased to a range of about 500-2800 psig, from about 1000-2000 psig, or from about 1500 to 2000 psig. The initial pH of the reaction in the absence of acid catalyst is in the range of 0 to 7 or in the range of 5 to 7.

When the acid content is eliminated or significantly reduced in the absence of water under the conditions of the above paragraph, a yield towards cellulosic sugar formation, ester formation, and derivatized sugar formation and away from the acid consuming peptide polymer breakdown is observed. In the presence of water as described in below and the absence of acid under the conditions of the above paragraph, ester formation from glycerides, FFAs, and phospholipids, sugar polymer breakdown, and peptide polymer breakdown are observed.

The reaction mixture before reaction can also contain water in an amount of at least about 3 wt % of the dry weight of the feedstock, at least about 5 wt % of the dry weight of the feedstock, at least about 10 wt % of the dry weight of the feedstock, at least about 30 wt % of the dry weight of the feedstock, at least about 40 wt % of the dry weight of the feedstock, or at least about 50 wt % of the dry weight of the feedstock. The reaction mixture before reaction preferably contains water in an amount from about 30 wt % to about 40 wt % of the dry weight of the feedstock.

The reactor system can be batch or continuous. There are several conventional pressure vessel systems available that will operate in batch and continuous modes and the process lends itself to the "conventional" methods for this stage. In addition, a continuous pipe-type reactor can be used to carry out the reaction. The reactor is a pipe with sufficient residence time to allow for the reaction to complete and is operated under the target pressure and temperature range. The pipe allows for reasonable reaction to occur with minimized vessel complexity.

The reaction can be carried out for a period of about 5 minutes to 120 minutes and the reaction time can depend on the selected reaction system and operating temperature. In a conventional stirred tank reactor, the reaction time can be in the range of 60 to 90 minutes for a batch reactor. At higher temperatures, and corresponding pressures, the reaction time can be reduced.

The reaction product slurry (6) typically consists of the algae pulp (containing cleaved cellulosic material, shortened peptides, and amino acids), crude biodiesel including unsaturated fatty acid alkyl esters, excess alcohol, catalyst, water and glycerin. The resulting biodiesel will be in the range of 10-50 wt % of the product slurry. The resulting peptides/amino acids will be in the range of 0-50 wt % of the product slurry. The resulting cleaved cellulosic materials will be in the range of 0-50 wt % of the product slurry. The reaction slurry is transferred to a Liquid/Solid Separation system. In this step, the liquid fraction is separated from the solids portion. Separation can be carried out using any number of standard separation techniques, such as filtration, centrifugation, combinations of each approach, and the like. Slight washing of the solids, in the separation device, can be carried out with a small amount of the alcohol (9A) recovered for recycle. The spent wash would then be added into the crude biodiesel (including unsaturated fatty acid alkyl esters).

The washed solids (7) are then sent to a demethylation step wherein the methanol (or other alcohol) is removed from the material via heating. Steam, from the aforementioned drying system, can be used for this step. The recovered alcohol (14) is transferred to the Methanol (Alcohol) Recovery System. The solids fraction (20) is transferred to, for example, the ethanol production portion of the process.

The crude biodiesel liquid, including unsaturated fatty acid alkyl esters, from the separation (8) is then sent to a Biodiesel Demethylation/Bottoms Separation system. In this process step, the liquid is first demethylated, i.e. alcohol removal, and the vaporized alcohol (9) sent to the Methanol (Alcohol) Recovery System. In the recovery system, the alcohol is distilled to eliminate traces of moisture then returned (15) to the reaction system for reuse.

When the alcohol is removed from the crude biodiesel liquid, the co-products, i.e. water and glycerin, separate from the biodiesel fraction. The catalyst reports to the aqueous/glycerin phase. This two phase system is then treated in a separation system, e.g. settling, centrifugation, and the like. The separated water/glycerin/catalyst is referred to as the "bottoms" fraction. This material (11) is transferred to a storage tank for subsequent disposition. Depending on the feedstock, the bottoms from the demethylation/bottoms separation step may contain high levels of protein-bearing materials. In this case, the protein-rich fraction can be sent to a separate surge and (if desirable) downstream processes for further separation of the protein fraction from the remainder of the material.

The demethylated biodiesel (including unsaturated fatty acid alkyl esters) (10) is then sent to the Biodiesel Distillation unit to fractionate the liquids from the solids. In this step, the biodiesel is heated to about 340° F. to 410° F. under full vacuum in, for example, a single stage, short path distillation unit. Under these conditions, the biodiesel fraction vaporizes and separates from the various lower volatility impurities in the liquid. The biodiesel vapor is then condensed using conventional indirect heat exchangers with cooling supplied by cooling water. The condensed biodiesel (12) is the transferred to biodiesel storage tanks where the material can be analyzed. The material can be further distilled under a high vacuum in the range of 750 mm to 755 mm Hg (vacuum) to separate the desired unsaturated fatty acid alkyl esters for further reactions as discussed below.

Optional Hydrolysis of Fatty Acid Alkyl Esters to form Free Fatty Acids

After direct esterification and distillation, the separated unsaturated fatty acid alkyl esters can be subjected to hydrolysis by mixing the esters with water at a water:ester mass ratio of 1:1 to 100:1, preferably 1:1 to 10:1 and a mineral acid catalyst such as $H_2SO_4$ or HCl at a catalyst:ester mass ratio of 0.01:1 to 1:1, preferably 0.01:1 to 0.1:1. Hydrolysis cleaves the alcohol group of the esters and converts the fatty acid alkyl esters to fatty acids. The temperature of the hydrolysis reaction is in the range of from about 50° C. to about 250° C., preferably from about 50° C. to about 100° C. The pressure of the hydrolysis reaction is in the range of from about 1 to about 100 bar, preferable from about 1 to about 10 bar.

The conversion of the fatty acid alkyl esters will generate two discrete phases, the top phase of the resulting system being fatty acids. The fatty acids are skimmed from the reaction vessel and transferred to an oxidation vessel for oxidation as discussed below.

Additional Method for Obtaining Unsaturated Fatty Acids

Unsaturated fatty acids can be extracted in low yield from the algae or another source using supercritical fluids or traditional solvent extraction. After extraction, non-free fatty acid lipids (e.g., triglycerides) can be converted using hydrolysis to fatty acids by exposing the lipid optionally to a base (OH$^-$) followed by an acid (H$^+$). Unsaturated free fatty acids (FFAs) can also be extracted from a source by mixing the source with a base and removing the FFAs as soaps using methods known in the art.

Additional sources of unsaturated fatty acids from traditional farm products include lard, butter, coconut oil palm oil, cottonseed oil, wheat germ oil, soya oil, olive oil, corn oil, sunflower oil, safflower oil, rapeseed oil, flaxseed, fish oil, and canola oil.

Unsaturated Fatty Acids or Unsaturated Fatty Acid Alkyl Esters

Unsaturated fatty acids for use in the present invention include carboxylic acids having an aliphatic chain containing at least one unsaturated C-C bond (i.e., at least C-C one double bond). Unsaturated fatty acid alkyl esters for use in the present invention include alkyl esters with an aliphatic chain as the carboxylate group containing at least one unsaturated C-C bond. The double bonds of the unsaturated fatty acid or unsaturated fatty acid alkyl ester can be either in the cis or trans conformation. Preferred unsaturated fatty acids or unsaturated fatty acid alkyl esters are fatty acids or fatty acid alkyl esters with the ability to create a high yield of malonic acid after oxidation of the double bonds. A high yield of malonic acid depends on the number and location of the double bonds. For example, a fatty acid with multiple double bonds each separated by two single bonds creates a high yield of malonic acid. The aliphatic chain of the fatty acid or unsaturated fatty acid alkyl ester is either branched or unbranched.

Unsaturated fatty acids or unsaturated fatty acid alkyl esters for use in the present invention can be naturally occurring or synthetic. Naturally occurring unsaturated fatty acids or unsaturated fatty acid alkyl esters include unsaturated fatty acids or unsaturated fatty acid alkyl esters where each double bond has 3 n carbon atoms after it, for some n, and all are cis bonds. Synthesized fatty acids or unsaturated fatty acid alkyl esters can include fatty acids or unsaturated fatty acid alkyl esters with trans bonds and can be produced via hydrogenation.

Unsaturated fatty acids suitable for the present invention include all-cis-7,10,13-hexadecatrienoic acid (16:3, cis,cis, cis-$\Delta^7,\Delta^{10},\Delta^{13}$), linoeic acid (18:2, cis,cis-$\Delta^9,\Delta^{12}$), α-linolenic acid (18:3, cis,cis,cis-$\Delta^9,\Delta^{12},\Delta^{15}$), gamma-linolenic acid (18:3, cis,cis,cis-$\Delta^6,\Delta^9,\Delta^{12}$), stearidonic acid (18:4, cis, cis,cis cis-$\Delta^6,\Delta^9,\Delta^{12},\Delta^{15}$), eicosadienoic acid (20:2, cis,cis-$\Delta^{11},\Delta^{14}$), mead acid (20:3, cis,cis,cis-$\Delta^5,\Delta^8,\Delta^{11}$), dihomo-gamma-linolenic acid (20:3, cis,cis,cis-$\Delta^8,\Delta^{11},\Delta^{14}$), eicosatrienoic acid (20:3, cis,cis,cis-$\Delta^{11},\Delta^{14},\Delta^{17}$), arachidonic acid (20:4, cis,cis,cis-$\Delta^5,\Delta^8,\Delta^{11},\Delta^{14}$), eicosatetraenoic acid (20:4, cis,cis,cis-$\Delta^8,\Delta^{11},\Delta^{14},\Delta^{17}$), eicosapentaenoic acid (EPA, 20:5, cis,cis,cis,cis,cis-$\Delta^5,\Delta^8,\Delta^{11},\Delta^{14},\Delta^{17}$), docosadienoic acid (22:2, cis,cis-$\Delta^{13},\Delta^{16}$), adrenic acid (22:4, cis,cis,cis,cis-$\Delta^7,\Delta^{10},\Delta^{13},\Delta^{16}$), docosapentaenoic acid (22:5, cis,cis,cis,cis,cis-$\Delta^7,\Delta^{10},\Delta^{13},\Delta^{16},\Delta^{19}$), docosahexaenoic acid (DHA, 22:6, cis,cis,cis,cis,cis,cis-$\Delta^4,\Delta^7,\Delta^{10},\Delta^{13},\Delta^{16},\Delta^{19}$), tetracosapentaenoic acid (24:5, cis,cis,cis,cis,cis-$\Delta^9,\Delta^{12},\Delta^{15},\Delta^{18},\Delta^{21}$), and tetracosahexaenoic acid (24:6, cis, cis,cis,cis,cis,cis-$\Delta^6,\Delta^9,\Delta^{12},\Delta^{15},\Delta^{18},\Delta^{21}$). Preferably, the unsaturated fatty acid is EPA, DHA, or a combination thereof.

Oxidation of Unsaturated Fatty Acids or Unsaturated Fatty Acid Alkyl Esters to a Malonic Acid Intermediate The unsaturated fatty acids or unsaturated fatty acid alkyl esters are oxidized using an oxidant at a molar ratio of oxidant to fatty acid of 1:1 to 100:1, preferably 1:1 to 10:1. The oxidant can be any oxidant in sufficient concentration to cleave at least one double bond of the unsaturated fatty acid to create 2 carboxylic acid groups, one on each of the resulting molecules. Examples of oxidants include oxygen, hydrogen peroxide, ozone, and potassium permanganate. Preferably, the oxidant is hydrogen peroxide or ozone. The temperature of the oxidation reaction is in the range of from about 50° C. to about 250° C., preferably from about 100° C. to about 200° C. The oxidation reaction can occur at a pressure of about 1 bar to about 150 bar preferbly from about 10 bar to about 50 bar.

Figure 4:
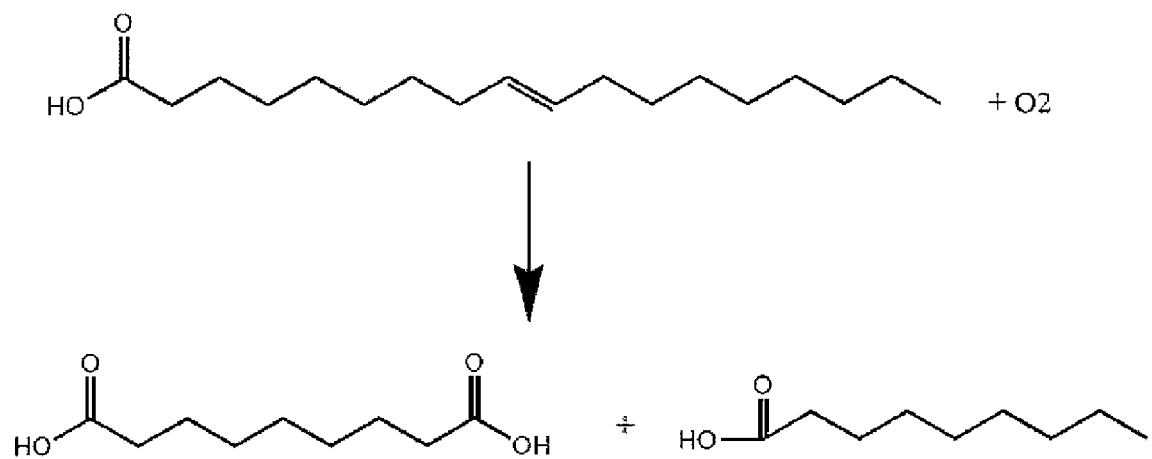
FIG. 4 shows the oxidation of oleic acid into a nonanedioic acid (azelaic acid) and a nonanoic acid (pelagonic acid) demonstrating the cleavage of the double bond in oleic acid to form 2 carboxylic acid groups.
Figure 5:
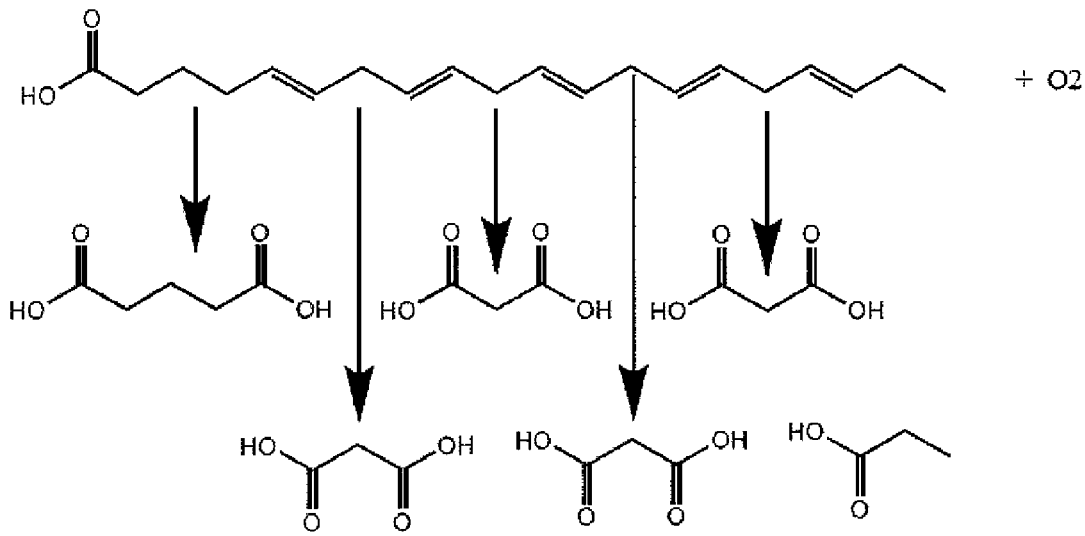
FIG. 5 shows the oxidation of EPA into 4 moles of malonic acid, 1 mole of propionic acid and 1 mole of glutaric acid followed by either the reduction of malonic acid into 1,3-PDO using hydrogen and a catalyst or the esterification of malonic acid into dimethyl malonate followed by the reduction of the dimethyl malonate using hydrogen and a catalyst to form 1,3-PDO.
Figure 5:
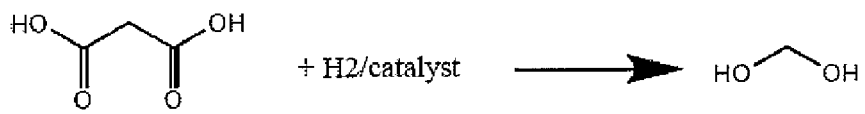
Figure 5:
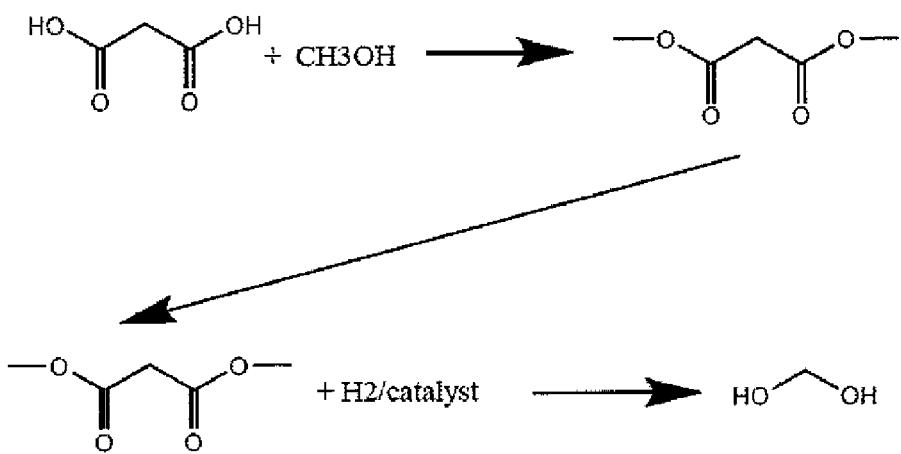

FIG. 4 demonstrates a typical oxidation reaction of this type. If EPA is the fatty acid, 4 moles of malonic acid, 1 mole of propionic acid and 1 mole of glutaric acid can be generated as show in FIG. 5. If DHA is the fatty acid, 5 moles of malonic acid, 1 mole of propionic acid and 1 mole of glutaric acid can be generated.

The resulting mix of fatty acids and diacids including malonic, propionic and glutaric acids are then transferred to an esterification vessel for esterification or the malonic acid is directly converted to 1,3-PDO as discussed below. Prior to esterification or conversion to 1,3-PDO, the malonic acid can be purified by ion exchange or continuous chromatography techniques known in the art.

Optional Esterification of the Diacids

The resulting diacids, including malonic acid, from the oxidation step can be subjected to a catalyzed esterification reaction using an alcohol and an acid catalyst to form diacid esters. The reaction is performed at a pH of about 0 to about 6 and, preferably, from about 1 to about 5. The reaction temperature is from about 150° C. to 260° C. or from about 200° C. to about 250° C., with a corresponding pressure that is sufficient to prevent boiling of the alcohol during the reaction stage, i.e. slightly in excess of the alcohol vapor pressure at the given temperature.

The alcohol can be a lower alcohol such as a group $C_{1-4}$ alcohol (e.g., methanol, ethanol, propanol, butanol, or mixtures thereof), and is preferably methanol or ethanol. The mass ratio of alcohol to diacid can be from, for example, 0.5:1 to 30:1 or 15:1 to 30:1. For methanol or ethanol, the pressure of the esterification reaction can range from about 1 bar to 150 bar, from about 25 bar to 75 bar and preferably from about 10 bar to 50 bar.

The acid catalyst for the reaction can be, for example, an inorganic acid (e.g., sulfuric acid, anhydrous hydrochloric acid, anhydrous nitric acid, boron trifluoride, and phosphoric acid), an organic acid (e.g. organic sulfonic acid), a solid phase catalyst (e.g., Envirocat™ EPZG, natural kaolinite clay, $B_2O_3/ZrO_2$, sulfated $SnO_2$, and zeolites), or combination thereof. The mass ratio of catalyst to diacid can be from 1:1 to 10:1. When the reaction mixture is a supercritical fluid, no catalyst is required. The esterification reaction typically is complete in less than 2 hours.

The diesters of the esterification reaction, including malonic diester (for example, dimethyl malonic ester, diethyl malonic ester, dibutyl malonic ester, dipropyl malonic ester, di-isobutyl malonic ester), are separated and then reduced as described below.

Reduction of the Malonic Acid or Malonic Diester to 1,3-propanediol (1,3-PDO)

Following the oxidation of fatty acids to yield malonic acid and, optionally, the subsequent esterification of the malonic acid as described above, the malonic acid or the malonic diester is reduced in the presence of a reducing agent and a reducing catalyst to generate 1,3-PDO.

Preferably, a mixture of hydrogen as the reducing agent and malonic acid or malonic diester is passed over a fixed bed reducing catalyst such as heterogeneous or homogenous copper chromium, copper chromite, ruthenium, Fe, Co, Cu, Pd, Zr, Ti, Th, V, Ta, Ag, Mo, Al, platinum, palladium Raney nickel, molybdenum, oxides of silicon, and silicates and oxides of zinc, zirconium, calcium, magnesium, aluminum, or combination thereof. Preferably, copper chromite or Raney nickel catalyst is used. Each mole of malonic diester or malonic acid is subsequently reduced to a diol. The mass ratio of catalyst to malonic acid or malonic diester is from 0.1:1 to 100:1, preferably the mass ratio of the catalyst to the malonic acid or malonic diester is from 0.1:1 to 1:1.

The molar ratio of the hydrogen to the malonic acid or malonic diester is from 1:1 to 1000:1, preferably the molar ratio of the hydrogen to the malonic acid is from 1:1 to 50:1. The hydrogen partial pressure of the reaction can be from about 1 bar to about 100 bars, preferably from about 1 bar to 50 bar. The total pressure of the reaction can be from about 0 to about 100 bar, preferably from about 0 to about 50 bar.

The temperature of the reaction is from about 40° C. to about 350° C., preferably from about 100° C. to about 250° C. The resulting 1,3-PDO is then condensed and separated from the system.

EXAMPLE

Conversion of EPA Into 1,3 PDO

EPA was oxidized using $H_2O_2$ at a mass ratio of 1:1 (EPA:$H_2O_2$) and at 200° C. for 1 to 60 minutes to yield malonic acid.

The malonic acid was then combined with alcohol at a molar ratio of 2.5:1 (alcohol to malonic acid) in the presence of an acidic catalyst, heated to 150-200° C. at a pressure of 25-75 bar, and allowed to react for 1-60 minutes to yield malonic diester.

Malonic diester was then mixed with hydrogen at a molar ratio of 10:1 ($H_2$ to malonic diester) in the presence of a catalyst at a temperature of 200-250° C. for 1-60 minutes to yield 1,3-PDO.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

What is claimed is:

1. A method for producing 1,3-propanediol from algae comprising
   (a) generating an unsaturated fatty acid alkyl ester by reacting the algae and an alcohol at a pH in a range of 0 to 7, at a temperature in a range of 140° C. to 300° C., and at a pressure in a range of 500 psig to 2800 psig,
   (b) optionally hydrolyzing the unsaturated fatty acid alkyl ester to an unsaturated fatty acid,
   (c) oxidizing the unsaturated fatty acid alkyl ester or the unsaturated fatty acid to generate malonic acid, and
   (d) reducing the malonic acid to generate 1,3-propanediol.

2. The method of claim 1, wherein the algae comprises unsaturated free fatty acids (FFAs), monoglycerides, diglycerides, triglycerides, phospholipids, or a combination thereof.

3. The method of claim 1, wherein the water content of the combination of the algae and alcohol before the reaction is from 30 wt % to 40 wt % of the dry weight of the algae.

4. The method of claim 1, further comprising adding a second fatty acid alkyl ester to the algae and alcohol before reacting.

5. The method of claim 1, wherein the alcohol is methanol or ethanol.

6. The method of claim 1, wherein the alcohol is in an amount from 50% to 320% molar excess of the contained oil in the algae.

7. The method according to claim 1, wherein generating the unsaturated fatty acid alkyl ester is performed without acid catalyst.

8. The method of claim 1, wherein the unsaturated fatty acid is eicosapentaenoic acid (EPA), docosahexaneoic acid (DHA), or a combination thereof.

9. The method of claim 1, wherein oxygen, hydrogen peroxide, ozone, or potassium permanganate is used to oxidize the unsaturated fatty acid alkyl ester or unsaturated fatty acid.

10. The method of claim 1, wherein hydrogen is used to reduce the malonic acid.

11. The method of claim 10, wherein the molar ratio of the hydrogen to the malonic acid is from 1:1 to 1000:1.

12. The method of claim 10, wherein the reduction is performed at a hydrogen partial pressure of from 1 bar to 100 bar.

13. The method of claim 1, wherein the reduction is performed at a temperature of from 40° C. to 350° C.

14. The method of claim 1, wherein a heterogeneous or homogenous copper chromium, copper chromite, ruthenium, Fe, Co, Cu, Pd, Zr, Ti, Th, V, Ta, Ag, Mo, Al, platinum, palladium Raney nickel, molybdenum, oxides of silicon, and silicates and oxides of zinc, zirconium, calcium, magnesium, aluminum, or a combination thereof is used as a reducing catalyst in the reduction of malonic acid.

15. The method of claim 1, wherein the unsaturated fatty acid alkyl ester is hydrolyzed to the unsaturated fatty acid.

16. The method of claim 1, wherein the unsaturated fatty acid alkyl ester is not hydrolyzed to the unsaturated fatty acid.

17. The method of claim 1, wherein the pH of step (a) is in the range of 5 to 7.

18. The method of claim 1, wherein the temperature of step (a) is in the range of 240° C. to 300° C.

19. The method of claim 1, wherein the pressure of step (a) is in the range of 1500 psig to 2000 psig.

20. A method for producing 1,3-propanediol from algae comprising
   (a) generating an unsaturated fatty acid alkyl ester by reacting the algae and an alcohol at a pH in a range of 5 to 7, at a temperature in a range of 240° C. to 300° C., and at a pressure in a range of 1500 psig to 2000 psig,
   (b) optionally hydrolyzing the fatty acid alkyl ester to an unsaturated fatty acid,
   (c) oxidizing the unsaturated fatty acid alkyl ester or the unsaturated fatty acid to generate malonic acid,
   (d) reacting the malonic acid with an alcohol and an acid catalyst to form malonic diester and
   (e) reducing the malonic diester to generate 1,3-propanediol.

* * * * *